(12) United States Patent
Yamamoto et al.

(10) Patent No.: US 8,026,394 B2
(45) Date of Patent: Sep. 27, 2011

(54) LITHIUM SALT AND METHOD FOR PRODUCING THEREOF

(75) Inventors: Hisashi Yamamoto, Chicago, IL (US); Masaki Matsui, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 283 days.

(21) Appl. No.: 12/447,961

(22) PCT Filed: Dec. 4, 2007

(86) PCT No.: PCT/JP2007/073405
§ 371 (c)(1),
(2), (4) Date: Jun. 15, 2009

(87) PCT Pub. No.: WO2008/069207
PCT Pub. Date: Jun. 12, 2008

(65) Prior Publication Data
US 2010/0036160 A1    Feb. 11, 2010

(30) Foreign Application Priority Data
Dec. 5, 2006  (JP) .................. 2006-328457

(51) Int. Cl.
C07F 9/22    (2006.01)
C07F 9/24    (2006.01)
C07F 9/26    (2006.01)
(52) U.S. Cl. ....................................... 564/14
(58) Field of Classification Search .......... 564/14
See application file for complete search history.

(56) References Cited

FOREIGN PATENT DOCUMENTS

| JP | 7-85888 | 3/1995 |
|---|---|---|
| JP | 10-189043 | 7/1998 |
| JP | 2001-68154 | 3/2001 |
| JP | 2008-1672 | 1/2008 |

OTHER PUBLICATIONS

K. Xu et al., "A New Protonation Chemistry of Phosphazenes and the Formation of bis(sulfonyl)imides," Inorganic Chemistry Communications, 1999, Vol. 2, No. 6, pp. 261-264 (1999).

*Primary Examiner* — Peter O Sullivan
(74) *Attorney, Agent, or Firm* — Finnegan, Henderson, Farabow, Garrett & Dunner, LLP

(57) ABSTRACT

A main object of the present invention is to provide a lithium salt which can improve its lithium transference number when used as a supporting salt of an electrolyte solution or the like. To attain the object, the present invention provides a lithium salt comprising a chemical structure represented by the following general formula (1):

General Formula (1)

$$R_1 - \underset{\underset{O}{\|}}{\overset{\overset{O}{\|}}{S}} - \overset{Li^+}{N^-} - \underset{\underset{N^-}{|}}{\overset{\overset{O}{\|}}{P}} - \overset{Li^+}{N^-} - \underset{\underset{O}{\|}}{\overset{\overset{O}{\|}}{S}} - R_3,$$

with additional group $O=\underset{\underset{R_2}{|}}{\overset{\overset{Li^+}{|}}{S}}=O$ in which R1 to R3 may be same or different from each other and denote a fluoroalkyl group, an alkyl group or a phenyl group.

6 Claims, 5 Drawing Sheets

LITHIUM SALT AND METHOD FOR PRODUCING THEREOF

CROSS-REFERENCE TO RELATED APPLICATIONS

This application is a national phase application of International Application No. PCT/JP2007/073405, filed Dec. 4, 2007, and claims the priority of Japanese Application No. 2006-328457, filed Dec. 5, 2006, the contents of both of which are incorporated herein by reference.

TECHNICAL FIELD

The present invention relates to a lithium salt which can be used as a supporting salt of an electrolyte solution or the like, and a method for producing the same.

BACKGROUND ART

Conventionally, electrolyte solutions in which lithium salts are dissolved in nonaqueous solvents have been used as electrolyte solutions for lithium secondary batteries. As lithium salts, substances such as $LiPF_6$ and $LiBF_4$ are generally known. Further, development of lithium secondary batteries using various kinds of lithium salts has been actively conducted currently.

For example, Patent Document 1 discloses a lithium secondary battery wherein an imide series lithium salt represented by a formula: $Li(C_nX_{2n+1}Y)_2N$ ("X" is halogen, "n" is an integer from 1 to 4, and "Y" is a CO group or a $SO_2$ group) is dissolved in a nonaqueous solvent. Further, Patent Document 2 discloses a lithium secondary battery wherein an imide series lithium salt represented by a formula: $LiN(C_mF_{2m+1}SO_2)(C_nF_{2n+1}SO_2)$ ("m" and "n" are each an independent integer from 1 to 4) is dissolved in a nonaqueous solvent. However, these lithium salts have a problem that their Li ionic transference numbers are low because they have only one Li cation contained in their respective molecular structures.

On the other hand, Patent Document 3 discloses a lithium secondary battery using a nonaqueous solvent wherein one or both of $LiPF_6$ or $LiBF_4$, and at least one substance from $Li_3PO_4$, $Li_2(OH)_3PO_4$, $Li(CH_3)_2PO_4$, and $Li_2(C_2H_5)PO_4$ are comprised as electrolytes. However, lithium phosphate salts having plural Li ions in their respective molecular structures as the case of $Li_3PO_4$ have a problem in general that their solubility to a solvent is low. Thus, it has been difficult to sufficiently improve their Li ionic transference number.

Patent Document 1: Japanese Patent Application Laid-Open (JP-A) No. 7-85888
Patent Document 2: JP-A No. 2001-68154
Patent Document 3: JP-A No. 10-189043

DISCLOSURE OF INVENTION

Problem to be Solved by the Invention

The present invention was achieved in view of the above-mentioned problems, and a main object thereof is to provide a lithium salt which can improve its lithium transference number when used as a supporting salt of an electrolyte solution or the like.

Means for Solving the Problems

To solve the problems, the present invention provides a lithium salt comprising a chemical structure represented by the following general formula (1):

[Chemical Formula 1]

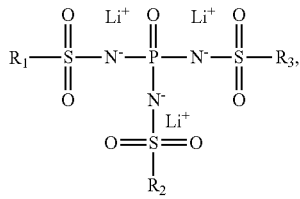

General Formula (1)

in which $R_1$ to $R_3$ may be same or different from each other and denote a fluoroalkyl group, an alkyl group or a phenyl group.

In the present invention, since the lithium salt obtained comprises three Li ions in its molecular structure, an electrolyte solution having a Li high ionic transference number can be obtained by using the lithium salt as a supporting salt of an electrolyte solution or the like.

Further, the present invention provides a lithium salt comprising a chemical structure represented by the following general formula (2):

[Chemical Formula 2]

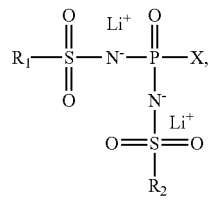

General Formula (2)

in which $R_1$ and $R_2$ may be same or different from each other and denote a fluoroalkyl group, an alkyl group or a phenyl group; and "X" denotes a halogen atom.

In the present invention, since the lithium salt obtained comprises two Li ions in its molecular structure, an electrolyte solution having a high Li ionic transference number can be obtained by using the lithium salt as a supporting salt of an electrolyte solution or the like.

The present invention further provides a method for producing a lithium salt comprising a synthesis step of synthesizing a lithium salt which has a chemical structure represented by the following general formula (1):

[Chemical Formula 5]

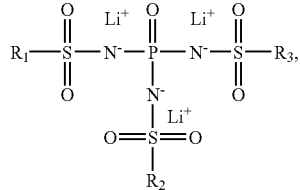

General Formula (1)

in which $R_1$ to $R_3$ may be same or different from each other and denote a fluoroalkyl group, an alkyl group or a phenyl group, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) to (3-3):

[Chemical Formula 3]

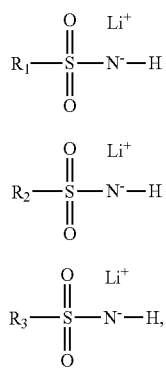

General Formula (3-1)

General Formula (3-2)

General Formula (3-3)

in which $R_1$ to $R_3$ may be same or different from each other and denote a fluoroalkyl group, an alkyl group or a phenyl group; and wherein the material B for synthesizing a lithium salt has a chemical structure represented by the following general formula (4):

[Chemical Formula 4]

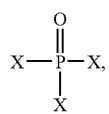

General Formula (4)

in which "X" denotes a halogen atom.

In the present invention, by carrying out the above-mentioned synthesis step, a lithium salt which can provide an electrolyte solution having a high Li ionic transference number, or a solid electrolyte membrane can be obtained.

The present invention further provides a method for producing a lithium salt comprising a synthesis step of synthesizing a lithium salt which has a chemical structure represented by the following general formula (2):

[Chemical Formula 8]

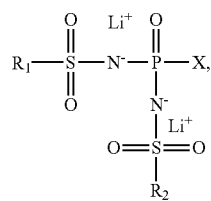

General Formula (2)

in which $R_1$ and $R_2$ may be same or different from each other and denote a fluoroalkyl group, an alkyl group or a phenyl group; and "X" denotes a halogen atom, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) and (3-2):

[Chemical Formula 6]

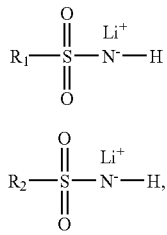

General Formula (3-1)

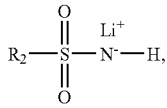

General Formula (3-2)

in which $R_1$ and $R_2$ may be same or different from each other and denote a fluoroalkyl group, an alkyl group or a phenyl group; and wherein the material B for synthesizing a lithium salt has a chemical structure represented by the following general formula (4):

[Chemical Formula 7]

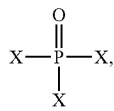

General Formula (4)

in which "X" denotes a halogen atom.

In the present invention, by carrying out the above-mentioned synthesis step, a lithium salt which can provide an electrolyte solution having a high ionic transference number, or a solid electrolyte membrane can be obtained.

The present invention preferably further comprising a purification step of removing a side reaction product generated by the synthesis step. This is because, an object substance having high purity can be obtained by carrying out purification even when a side reaction product is generated by the synthesis step.

Effect of the Invention

The present invention attains an effect of providing a novel lithium salt which is useful for a usage such as a supporting salt of an electrolyte solution.

BEST MODE FOR CARRYING OUT THE INVENTION

Figure 1:
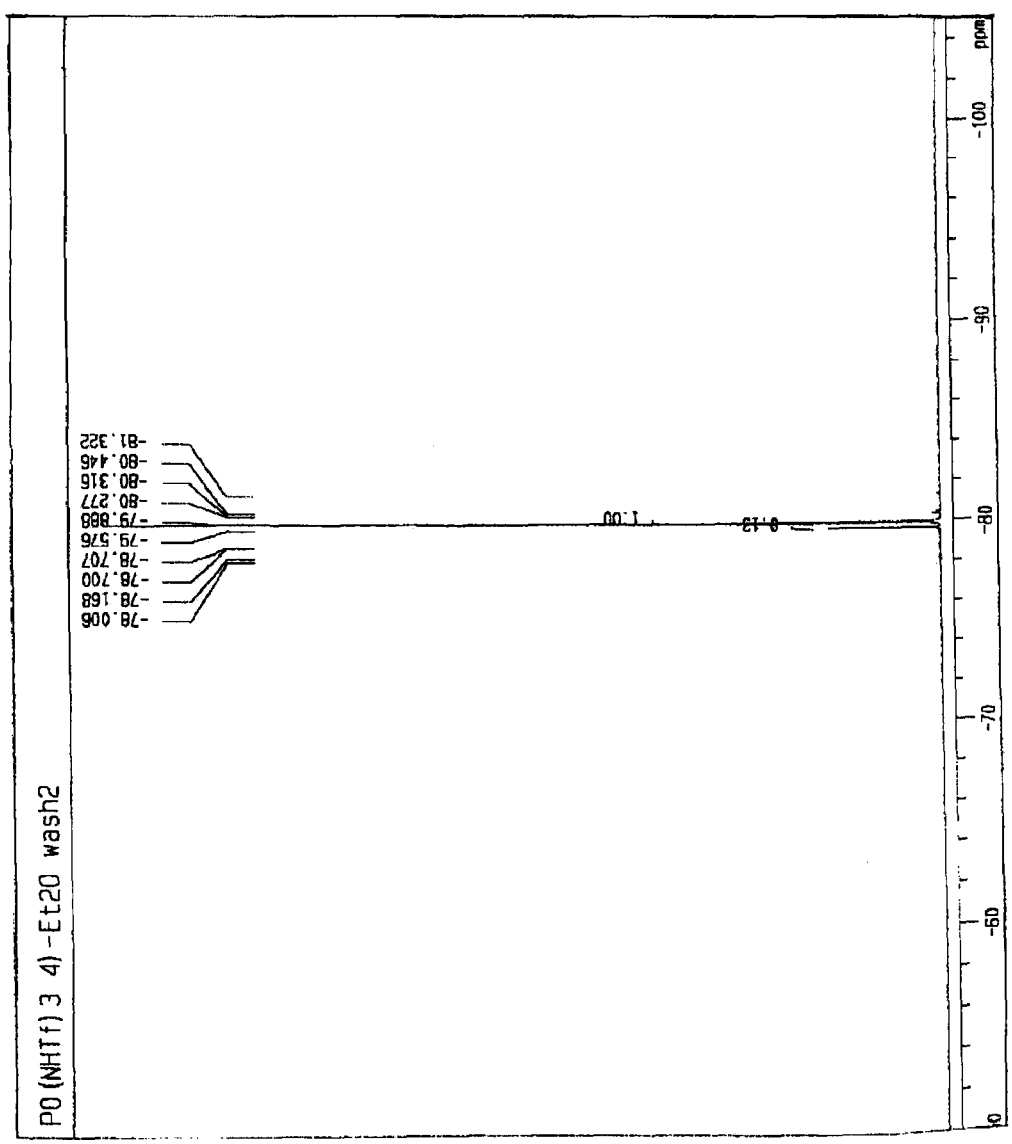
FIG. 1 is a $^{19}$F-NMR chart of the tri-substituted lithium salt obtained by the Synthesizing Example.

Hereinafter, the lithium salt and the method for producing the same of the present invention will be described in detail.

A. Lithium Salt

First, the lithium salt of the present invention will be explained. The lithium salt of the present invention is roughly classified to: a lithium salt having a chemical structure represented by the general formula (1) (first embodiment), and a lithium salt having a chemical structure represented by the general formula (2) (second embodiment). Hereinafter, the lithium salt of the present invention will be explained by each embodiment.

1. First Embodiment

First, a first embodiment of the lithium salt of the present invention will be explained. A lithium salt of the present embodiment has a chemical structure represented by the above-mentioned general formula (1).

In the present embodiment, since the lithium salt obtained has three Li ions in its molecular structure, an electrolyte solution having a high Li ionic transference number can be obtained by using the lithium salt as a supporting salt of an electrolyte solution or the like. The lithium phosphate salts having plural Li ions in their respective molecular structures as the case of $Li_3PO_4$ have a problem in general that their solubility to a solvent is low. However, the lithium salt of the present embodiment can be dissolved into a specific solvent mentioned later and thus, can be used as a supporting salt of an electrolyte solution. Further, the lithium salt of the present embodiment can also be used as a solid electrolyte without being dissolved into a solvent.

In the general formula (1), $R_1$ to $R_3$ may be same or different from each other. In the present embodiment, it is preferable that at least two out of $R_1$ to $R_3$ are the same functional group, and more preferable that all of $R_1$ to $R_3$ are the same functional group. Thereby, production of the lithium salt becomes easy.

In the general formula (1), $R_1$ to $R_3$ denote a fluoroalkyl group, an alkyl group or a phenyl group. In the present embodiment, it is preferable that at least one of $R_1$ to $R_3$ is a fluoroalkyl group, and more preferable that all of $R_1$ to $R_3$ are fluoroalkyl groups.

The fluoroalkyl group(s) may be the one in which all hydrogen in the alkyl group are substituted with fluorine, or may be the one in which a part of hydrogen is substituted with fluorine. Further, the number of carbon atoms of the fluoroalkyl group(s) is preferably within the range of 1 to 4. In the present embodiment, it is particularly preferable that the fluoroalkyl group(s) is —$CF_3$.

The alkyl group may be a straight chain alkyl group or a branched-chain alkyl group. Further, the number of carbon atoms of the alkyl group is not particularly limited, but it is preferably within the range of 1 to 4. The alkyl group may be —$CH_3$ for example.

The phenyl group generally has hydrogen bound to a benzene ring. In the present embodiment, the hydrogen may be a fluorine-substituted phenyl group in which the hydrogen is substituted with fluorine. In other words, the above-mentioned "R" may be a fluorine-substituted phenyl group. As an example of the fluorine-substituted phenyl group, —$C_6F_5$ can be cited.

In particular, in the present embodiment, it is preferable that the lithium salt has a chemical structure represented by a formula (1-1).

[Chemical Formula 9]

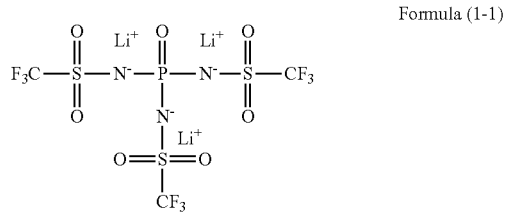

Formula (1-1)

The lithium salt of the present embodiment can be dissolved into a solvent such as propylene carbonate. Thus, it is useful as a supporting salt for an electrolyte solution. Thus obtained electrolyte solution can be used for a general electrochemical device such as a primary battery, a secondary battery, an electrolytic capacitor and an electric double layer capacitor. Further, the lithium salt of the present embodiment can be used as a solid electrolyte of the above-mentioned electrochemical devices. The lithium salt of the present embodiment can be identified by $^{19}F$-NMR, $^{31}P$-NMR, plasma emission spectrometry (ICP) and the like.

2. Second Embodiment

Next, a second embodiment of the lithium salt of the present invention will be explained. A lithium salt of the present embodiment has a chemical structure represented by the above-mentioned general formula (2).

In the present embodiment, since the lithium salt obtained has two Li ions in its molecular structure, an electrolyte solution having a high Li ionic transference number can be obtained by using the lithium salt as a supporting salt of an electrolyte solution or the like. The lithium phosphate salts having plural Li ions in their respective molecular structures as the case of $Li_3PO_4$ have a problem in general that their solubility to a solvent is low. However, the lithium salt of the present embodiment can be dissolved into a specific solvent mentioned later and thus, can be used as a supporting salt of an electrolyte solution. Further, the lithium salt of the present embodiment can also be used as a solid electrolyte without being dissolved into a solvent.

In the general formula (2), $R_1$ and $R_2$ may be same or different from each other. In the present embodiment, it is preferable that $R_1$ and $R_2$ are the same functional group. Thereby, production of the lithium salt becomes easy.

In the general formula (2), $R_1$ and $R_2$ denote a fluoroalkyl group, an alkyl group or a phenyl group. In the present embodiment, it is preferable that $R_1$ and $R_2$ are fluoroalkyl groups. As the above-mentioned fluoroalkyl group(s), alkyl group and phenyl group are the same as those explained in the above "1. First Embodiment", explanations are omitted here. In particular, in the present embodiment, the fluoroalkyl group(s) is preferably —$CF_3$.

In the general formula (2), "X" denotes a halogen atom. As examples of the halogen atom, a fluorine atom (F), a chlorine atom (Cl), a bromine atom (Br), an iodine atom (I) can be cited. Among them, in the present embodiment, it is preferable that "X" is a halogen atom which is heavier than a chlorine atom (Cl), and more preferable that "X" is a chlorine atom (Cl).

In particular, in the present embodiment, it is preferable that the lithium salt has a chemical structure represented by a formula (2-1). It is confirmed that such lithium salt has higher solubility to an organic solvent than that of the lithium salt represented by the above-mentioned formula (1-1).

[Chemical Formula 10]

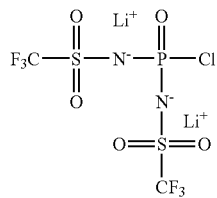

Formula (2-1)

The lithium salt of the present embodiment can be dissolved into a solvent such as propylene carbonate. Thus, it is useful as a supporting salt for an electrolyte solution. Thus obtained electrolyte solution can be used for a general electrochemical device such as a primary battery, a secondary battery, an electrolytic capacitor and an electric double layer capacitor. Further, the lithium salt of the present embodiment can be used as a solid electrolyte of the above-mentioned electrochemical devices. The lithium salt of the present embodiment can be identified by $^{19}$F-NMR, $^{13}$P-NMR, plasma emission spectrometry (ICP) and the like.

3. Others

The present invention provides a lithium salt comprising a chemical structure represented by the following general formula (5):

[Chemical Formula 11]

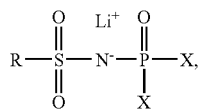

General Formula (5)

in which "R" denotes a fluoroalkyl group, an alkyl group or a phenyl group; and "X" denotes a halogen atom.

As the fluoroalkyl group, the alkyl group, the phenyl group and the halogen atom of the general formula (5) are the same as the above "2. Second Embodiment", explanations are omitted here. In the present invention, it is preferable that "R" is —$CF_3$, and "X" is a chlorine atom (Cl).

B. Method for Producing a Lithium Salt

Next, a method for producing a lithium salt of the present invention will be explained. The method for producing a lithium salt of the present invention can be roughly classified into: a method for producing a lithium salt having a chemical structure represented by a general formula (1) (third embodiment), and a method for producing a lithium salt having a chemical structure represented by a general formula (2) (fourth embodiment). Hereinafter, the method for producing a lithium salt of the present invention will be explained by each embodiment.

1. Third Embodiment

First, a third embodiment of the method for producing a lithium salt of the present invention will be explained. The lithium salt of the present embodiment comprises a synthesis step of synthesizing a lithium salt which has a chemical structure represented by the following general formula (1):

[Chemical Formula 14]

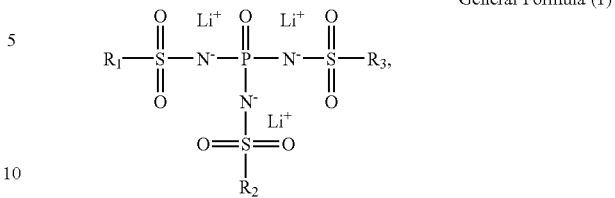

General Formula (1)

in which $R_1$ to $R_3$ may be same or different from each other and denote a fluoroalkyl group, an alkyl group or a phenyl group, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) to (3-3):

[Chemical Formula 12]

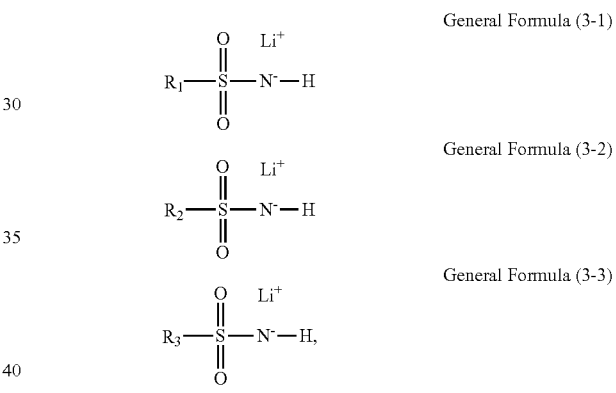

in which $R_1$ to $R_3$ may be same or different from each other and denote a fluoroalkyl group, an alkyl group or a phenyl group; and wherein the material B for synthesizing a lithium salt has a chemical structure represented by the following general formula (4):

[Chemical Formula 13]

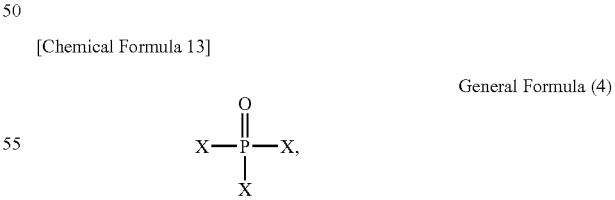

General Formula (4)

in which "X" denotes a halogen atom.

In the present embodiment, a lithium salt which can provide an electrolyte solution having a high Li ionic transference number or a solid electrolyte membrane can be obtained by carrying out the above-mentioned synthesis step.

Next, one example of the method of producing a lithium salt of the present embodiment will be explained with a reference to the reactions 1 and 2 shown below.

[Chemical Formula 15]

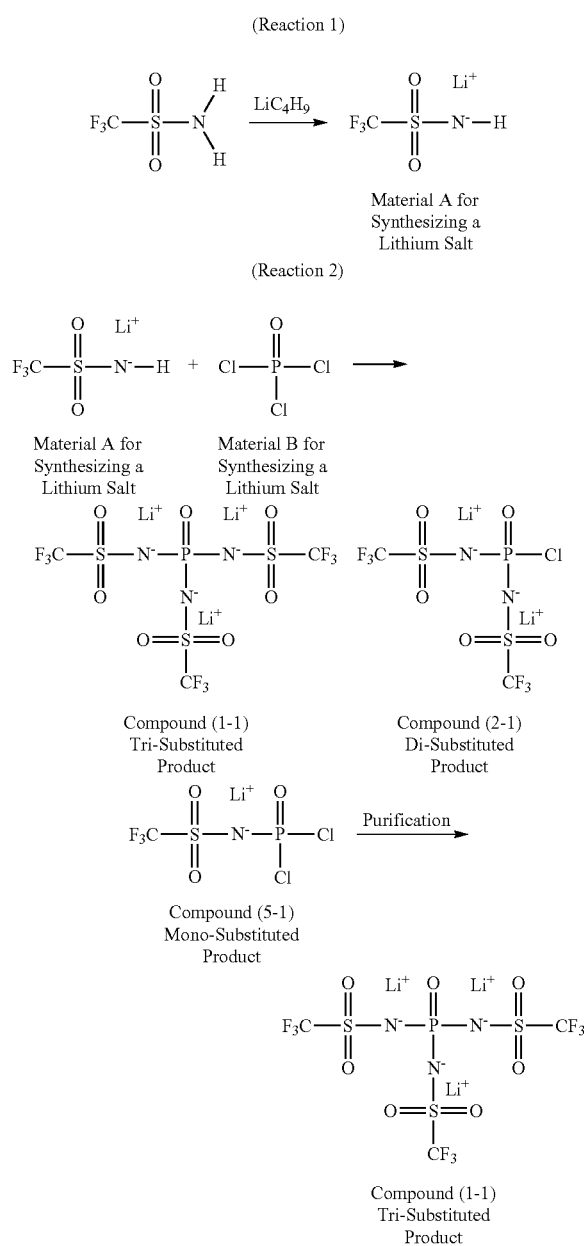

The reaction 1 is a reaction to obtain a material A for synthesizing a lithium salt by: preparing a solution in which trifluoromethanesulfonamide ($CF_3SO_2NH_2$) is dissolved into an organic solvent such as diethyl ether under an inert gas atmosphere such as Ar, and adding a basic lithium compound such as n-butyllithium ($LiC_4H_9$) while stirring the solution in an ice bath. As mentioned later, the lithium salt may be synthesized by using a single material A for synthesizing a lithium salt or by using plural materials A for synthesizing a lithium salt.

The reaction 2 is a reaction generated by: preparing a solution in which phosphoric trichloride ($POCl_3$, material B for synthesizing a lithium salt) is dissolved into an organic solvent such as diethyl ether under an inert gas atmosphere such as Ar, and adding the material A for synthesizing a lithium salt obtained in the reaction 1 while stirring the solution in an ice bath. By reaction 2, a tri-substituted product (compound (1-1)) wherein three ($CF_3SO_2NLi$) groups are bound to a P atom is synthesized. This is the object substance of the present embodiment. However, since the reaction 2 is a reaction substituting the Cl atom of $POCl_3$ with $CF_3SO_2NLi$ groups, a di-substituted product (compound (2-1)) and a mono-substituted product (compound 5-1) may be generated as side reaction products in some cases. In such cases, by carrying out a purification step of removing the generated side reaction products utilizing for example a difference in solubility to the solvent used, an object substance (compound (1-1)) having high purity can be obtained.

Hereinafter, the method of producing a lithium salt of the present embodiment will be explained by each step.

(1) Synthesis Step

First, a synthesis step of the present embodiment will be explained. The synthesis step of the present embodiment is a step of synthesizing the lithium salt which has a chemical structure represented by the above-mentioned general formula (1) by using and reacting: the material A for synthesizing a lithium salt which has a chemical structure represented by the above-mentioned general formulae (3-1) to (3-3), and the material B for synthesizing a lithium salt which has a chemical structure represented by the above-mentioned general formula (4).

The material A for synthesizing a lithium salt used in the present embodiment is a material having a chemical structure represented by the above-mentioned general formulae (3-1) to (3-3). As $R_1$ to $R_3$ shown in the general formulae (3-1) to (3-3) are the same as those described in the above "A. Lithium Salt 1. First Embodiment", explanations are omitted here. In particular, in the present embodiment, it is preferable that $R_1$ to $R_3$ are the same functional group, that is, the compounds represented by the general formulae (3-1) to (3-3) are the same compounds. Further, it is preferable that $R_1$ to $R_3$ are fluoroalkyl groups and they are $-CF_3$.

The material B for synthesizing a lithium salt used in the present embodiment has a chemical structure represented by the above-mentioned general formula (4). As "X" is the same as that of the general formula (2) described in the above "A. Lithium Salt 2. Second Embodiment", an explanation is omitted here. In particular, in the present embodiment, it is preferable that "X" is a chlorine atom (Cl).

A solvent used in the reaction is not particularly limited as long as the materials A and B for synthesizing a lithium salt can dissolved into. As a specific example, diethyl ether, tetrahydrofuran (THF), ethanol and methanol can be cited.

A reaction temperature for the materials A and B for synthesizing a lithium salt is not particularly limited, and it is preferably within the range of −10° C. to 5° C. for example. In particular, in the present embodiment, it is preferably a temperature at which the materials A and B for synthesizing a lithium salt can react when they are placed in the ice bath.

Respective amount of the materials A and B for synthesizing a lithium salt used is not particularly limited as long as the lithium salt represented by the general formula (1) can be obtained. For example, when the amount of the material B for synthesizing a lithium salt used is made as 1, the amount of the material A for synthesizing a lithium salt is preferably within the range of 3 to 15, more preferably within the range of 5 to 9, on molar basis.

In method for producing a lithium salt of the present embodiment, depending on synthesizing conditions applied, a mixture of a tri-substituted product, a di-substituted product and a mono-substituted product of ($RSO_2NLi$) group may be obtained in some cases as shown in the above-mentioned reaction 2. To obtain in the synthesis step at high rate the lithium salt represented by the general formula (1), i.e., the tri-substituted product of (RSO₂NLi) group, it is preferable to add the material A for synthesizing a lithium salt to the material B for synthesizing a lithium salt by 5 equivalent weight or more. Incidentally, when the material A for synthesizing a lithium salt is less than 3 equivalent weight for example, it is assumed that TfNH₂ and phosphorus amide are generated because N—H of phosphorus amide is acidized and H—Li exchange occurs.

As details of the lithium salt represented by the general formula (1) obtained in the present embodiment are the same as those explained in the above "A. Lithium Salt 1. First Embodiment", explanations are omitted here.

(2) Purification Step

Next, a purification step of the present embodiment will be explained. In the present embodiment, it is preferable to carry out a purification step to remove a side reaction product generated in the above-mentioned synthesis step. Thereby, an object substance having high purity can be obtained even in the case when a side reaction product is generated in the synthesis step.

As an example of a method to remove the side reaction product, a method of utilizing a difference in solubility can be cited. As examples of a solvent used in the method of utilizing a difference in solubility, diethyl ether, alcohols, acetone, acetic acid, hexane, cyclohexane, pentane, water, chloroform, benzene, acetic ether, methyl propionate, pyridine, and dimethylformamide can be cited. In the present embodiment, it is preferable to purify the lithium salt by arbitrarily conducting a solubility test using the above-mentioned solvents, and selecting a solvent most suitable in separating a main reaction product and a side reaction product.

For example, when the above-mentioned reactions 1 and 2 are made, a mixture of lithium salt which comprises a tri-substituted product and a di-substituted product of (CF₃SO₂NLi) group but hardly any mono-substituted product thereof may be obtained in some cases. In such cases, as the tri-substituted product has low solubility to diethyl ether and the di-substituted product has high solubility to diethyl ether, suspension cleaning of the obtained mixture of lithium salt is conducted using diethyl ether. Thereby, the tri-substituted product remains to the suspended material and the di-substituted product is contained into the suspension so that both products can be separated.

2. Fourth Embodiment

Next, a fourth embodiment of the method for producing a lithium salt of the present invention will be explained. The method for producing a lithium salt of the present embodiment comprises a synthesis step of synthesizing a lithium salt which has a chemical structure represented by the following general formula (2):

[Chemical Formula 18]

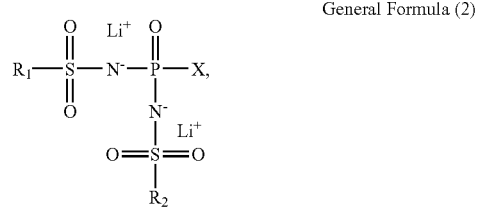

General Formula (2)

in which $R_1$ and $R_2$ may be same or different from each other and denote a fluoroalkyl group, an alkyl group or a phenyl group; and "X" denotes a halogen atom, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) and (3-2):

[Chemical Formula 16]

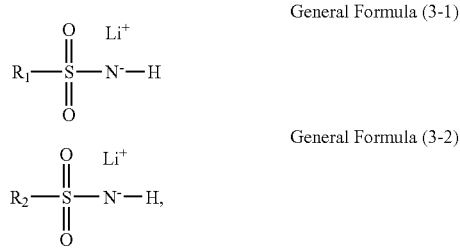

in which $R_1$ and $R_2$ may be same or different from each other and denote a fluoroalkyl group, an alkyl group or a phenyl group; and wherein the material B for synthesizing a lithium salt has a chemical structure represented by the following general formula (4):

[Chemical Formula 17]

General Formula (4)

in which "X" denotes a halogen atom.

In the present embodiment, a lithium salt which can provide an electrolyte solution having a high Li ionic transference number or a solid electrolyte membrane can be obtained by carrying out the above-mentioned synthesis step.

As specific examples of the method for producing a lithium salt of the present embodiment are the same as those in principle to the above-mentioned reactions 1 and 2, explanations are omitted here. Hereinafter, the method for producing a lithium salt of the present embodiment will be explained by each step.

(1) Synthesis Step

A synthesis step of the present embodiment is a step of synthesizing the lithium salt which has a chemical structure represented by the above-mentioned general formula (2) by using and reacting: the material A for synthesizing a lithium salt which has a chemical structure represented by the above-mentioned general formulae (3-1) and (3-2), and the material B for synthesizing a lithium salt which has a chemical structure represented by the above-mentioned general formula (4).

As materials A and B for synthesizing a lithium salt, a solvent used in reactions and others are the same as those explained in the above "1. Third Embodiment", explanations are omitted here. In particular, in the present embodiment, it is preferable that $R_1$ and $R_2$ are the same functional group, that is, the compounds represented by the general formulae (3-1) and (3-2) are the same compounds. Further, it is preferable that $R_1$ and $R_2$ are fluoroalkyl groups and they are —$CF_3$. Further, in the present embodiment, it is preferable that "X" is a chlorine atom (Cl).

In the method for producing a lithium salt of the present embodiment, depending on synthesizing conditions applied, a mixture of a di-substituted product, a tri-substituted product and a mono-substituted product of ($RSO_2NLi$) group may be obtained in some cases as shown in the above-mentioned reaction 2. To obtain in the synthesis step at high rate the lithium salt represented by the general formula (2), i.e., the di-substituted product of ($RSO_2NLi$) group, it is preferable for example to add the material A for synthesizing a lithium salt to the material B for synthesizing a lithium salt by the amount within the range of 2 to 10, and more preferably within the range of 4 to 9 when an amount of the material B for synthesizing a lithium salt is made 1.

As details of the lithium salt represented by the general formula (1) obtained in the present embodiment are the same as those explained in the above "A. Lithium Salt 2. Second Embodiment", explanations are omitted here.

(2) Purification Step

Next, a purification step of the present embodiment will be explained. In the present embodiment, it is preferable to carry out a purification step to remove a side reaction product generated in the above-mentioned synthesis step. Thereby, an object substance having high purity can be obtained even in the case when a side reaction product is generated in the synthesis step. As factors such as a specific purification method are the same as those explained in the above "1. Third Embodiment", explanations are omitted here.

Further, in the present invention, by appropriately adjusting synthesizing conditions or purification conditions, a method for producing a lithium salt having a chemical structure represented by the above-mentioned general formula (5), i.e., a mono-substituted product of a ($CF_3SO_2NLi$) group can be provided.

The present invention is not limited to the embodiments described above. The embodiments described above are mere illustrative, and those having substantially the same constitution and the same working effect as in the technical idea described in the claims of the present invention are included in the technical scope of the present invention.

EXAMPLES

Hereinafter, the present invention is described in more detail by reference to the Examples.

Synthesizing Example

A lithium salt was synthesized according to the above-mentioned reactions 1 and 2.
(Reaction 1)

First, 2.0 g of $CF_3SO_2NH_2$ (manufactured by Sigma-Aldrich Japan K.K) was dissolved under Ar atmosphere into a 20 ml of a dehydro-diethyl ether solution and a solution was obtained. Next, n-butyllithium/hexane (1.59 M, 8.45 ml, manufactured by Sigma-Aldrich Japan K.K.) was slowly added to the resultant solution while stirring the solution in an ice bath. Subsequently, temperature of the solution was raised to room temperature and thereby a solution containing a material A for synthesizing a lithium salt was obtained.
(Reaction 2)

Next, 0.19 ml of $POCl_3$ (manufactured by Sigma-Aldrich Japan K.K) was mixed under Ar atmosphere with a 20 ml of a dehydro-diethyl ether solution and a solution was obtained. Subsequently, the above-mentioned solution containing a material A for synthesizing a lithium salt was slowly dropped to the resultant solution while stirring the solution in an ice bath.

Thereafter, temperature of the solution was raised to room temperature, 20 ml of THF and 20 ml of dimethoxyethane were added to the resultant solution to progress the reaction, and the solution was heated to reflux at 50° C. for 12 hours.

The solvent of the obtained solution was removed under reduced pressure and then dried and solidified. Next, suspension cleaning was carried out in order of diethyl ether, chloroform and diethyl ether, and a white crystal compound (1-1) was thereby obtained. Further, the second suspension of diethyl ether used in the suspension cleaning was vacuum concentrated and dried, and a compound (2-1) of white to light yellow powder was obtained. Under these conditions, a lithium salt of mono-substituted product (compound (5-1)) was hardly obtained.
(Identification of Lithium Salt)

Figure 2:
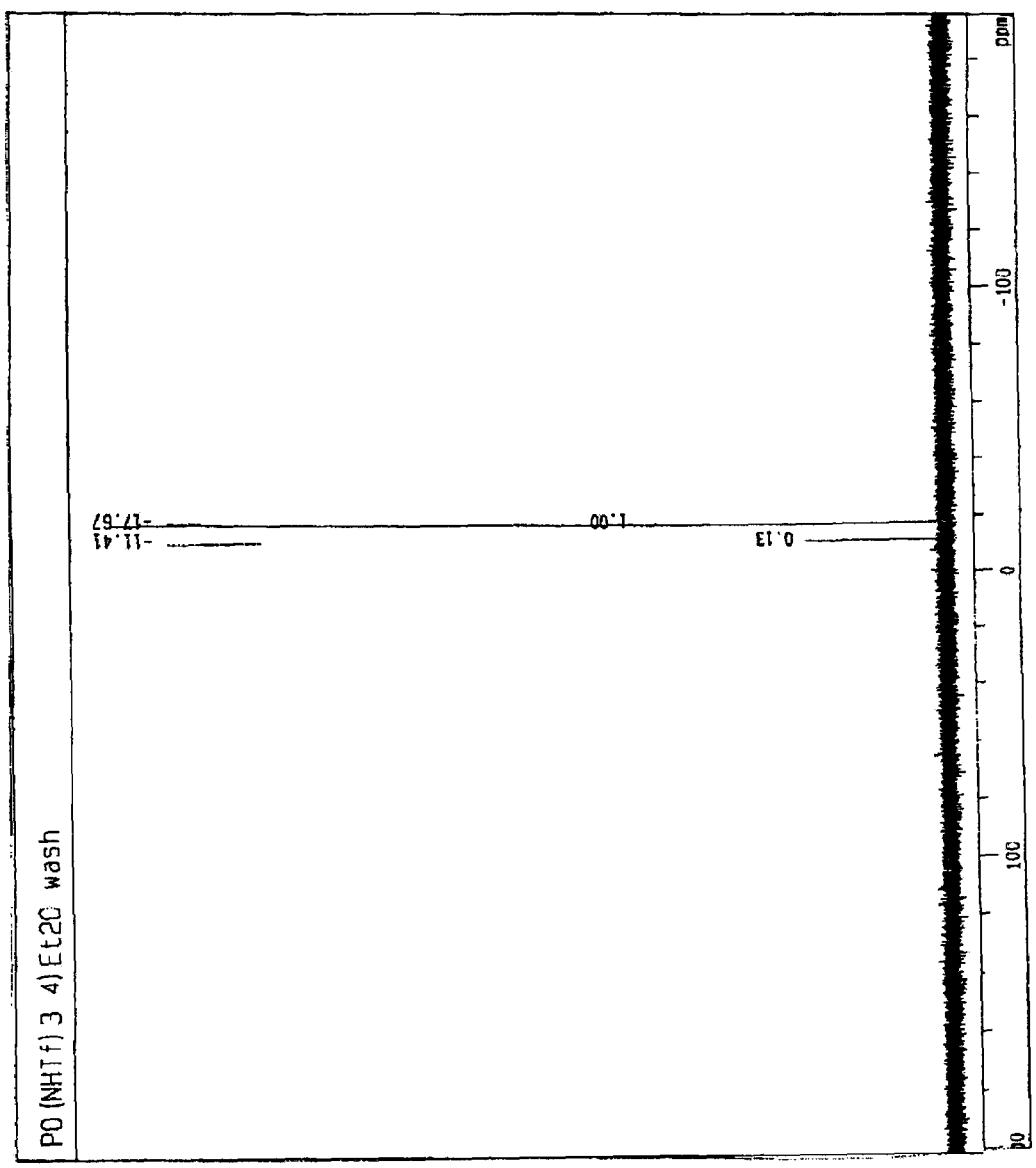
FIG. 2 is a $^{31}$P-NMR chart of the tri-substituted lithium salt obtained by the Synthesizing Example.
Figure 3:
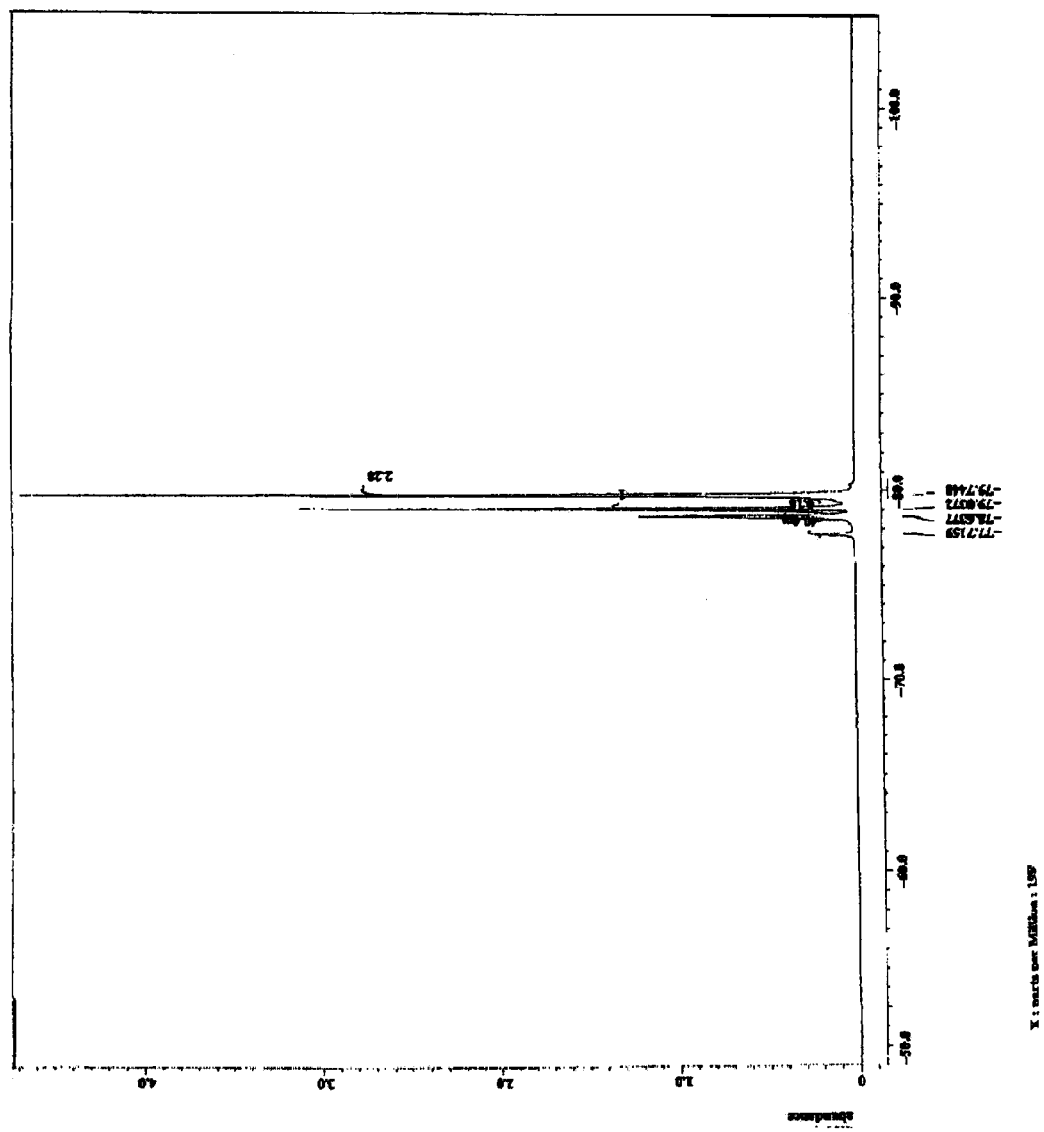
FIG. 3 is a $^{19}$F-NMR chart of the di-substituted lithium salt obtained by the Synthesizing Example.
Figure 4:
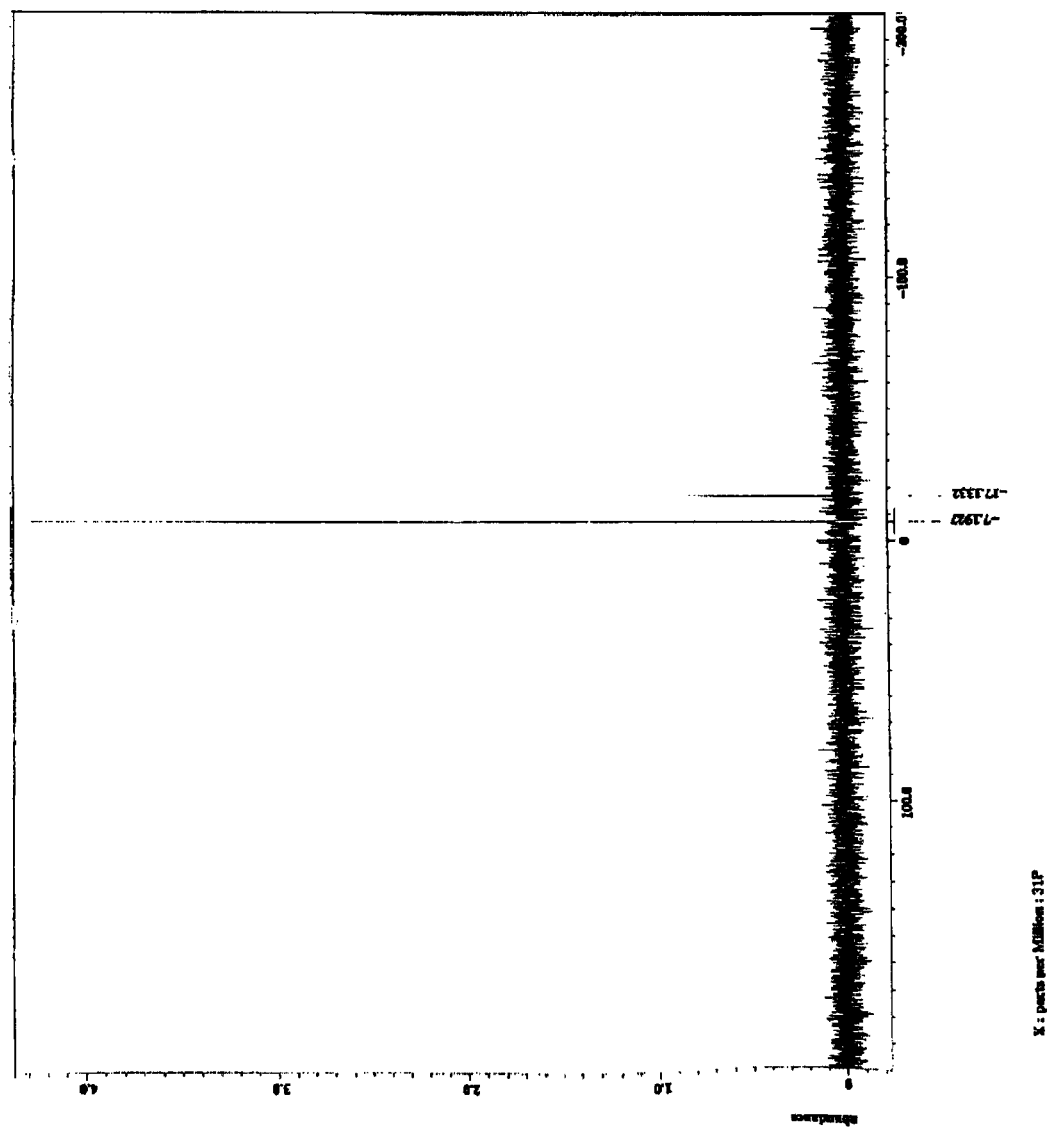
FIG. 4 is a $^{31}$P-NMR chart of the di-substituted lithium salt obtained by the Synthesizing Example.

Results of $^{19}$F-NMR and $^{31}$P-NMR of the compound (1-1), which is a tri-substituted product, are shown in FIGS. 1 and 2. Results of $^{19}$F-NMR and $^{31}$P-NMR of the compound (2-1), which is a di-substituted product, are shown in FIGS. 3 and 4.

Examples 1-3

The lithium salt of tri-substituted product (Compound (1-1)) obtained in the Synthesizing Example was dissolved into propion carbonate so as to make electrolyte solutions having densities of 0.5 M, 1.0 M and 1.5 M. It was confirmed that the lithium salt of all the electrolyte solutions were completely dissolved.

Figure 5:
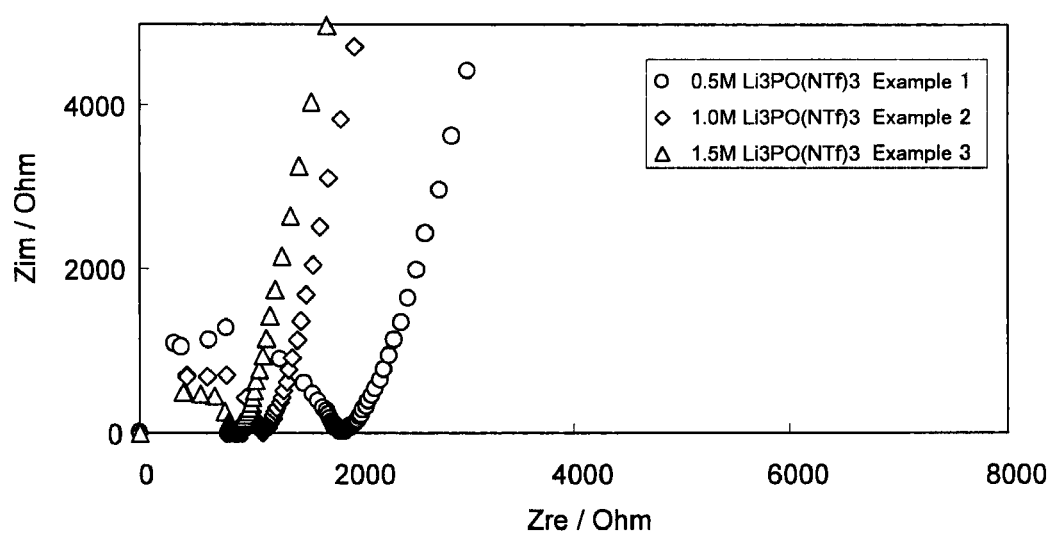
FIG. 5 is a graph showing the results of impedance measurement of electrolyte solutions containing tri-substituted lithium salts.

Ion conductivity of the respective electrolyte solutions obtained was measured using an alternating-current impedance method. A biopolar cell having platinum/platinized electrodes facing each other was used in measuring ion conductivity, and impedance was measured at 1 MHz to 1 Hz. The ion conductivity of the respective electrolyte solutions were calculated from the obtained resistance values and cell constant. Results are shown in Table 1. Further, FIG. 5 is a graph showing the results of impedance measurement of the respective electrolyte solutions.

Comparative Examples 1 and 2

Electrolyte solutions were obtained by dissolving $Li_3PO_4$ into propion carbonate so as to make densities thereof 0.5 M and 1.0M. The obtained electrolyte solutions were suspended and $Li_3PO_4$ were not completely dissolved.

Conductivity of the respective electrolyte solutions were measured in the same manner as in Example 1 except that the obtained electrolyte solutions were used. Results are shown in Table 1.

TABLE 1

| | Lithium Salt | Density of Lithium Salt | Dissolved State | Conductivity $Scm^{-1}$ |
|---|---|---|---|---|
| Example 1 | tri-substituted product | 0.5M | Completely-Dissolved | $5.45 \times 10^{-4}$ |
| Example 2 | tri-substituted product | 1.0M | Completely-Dissolved | $8.81 \times 10^{-4}$ |
| Example 3 | tri-substituted product | 1.5M | Completely-Dissolved | $1.14 \times 10^{-3}$ |
| Comparative Example 1 | $Li_3PO_4$ | 0.5M | Suspended | $1.75 \times 10^{-6}$ |
| Comparative Example 2 | $Li_3PO_4$ | 1.0M | Suspended | $1.09 \times 10^{-6}$ |

In the respective electrolyte solutions of Examples 1 to 3, the lithium salts were completely dissolved into propion carbonate. It was also confirmed that these electrolyte solutions show good conductivity. On the other hand, in the respective electrolyte solutions of Comparative Examples 1 and 2, the lithium salts did not dissolve into propion carbonate at all and conductivities of the electrolyte solutions were low.

The invention claimed is:

1. A lithium salt comprising a chemical structure represented by the following general formula (1):

[Chemical Formula 1]

$$R_1-\underset{\underset{O}{\overset{O}{\|}}}{S}-N^--\underset{\underset{\underset{\underset{R_2}{|}}{\underset{S}{|}}}{\underset{O=S=O}{|}}}{\overset{Li^+}{|}}\overset{O}{\overset{\|}{P}}-N^--\underset{\underset{O}{\overset{O}{\|}}}{S}-R_3 \quad \text{General Formula (1)}$$

in which $R_1$ to $R_3$ may be same or different from each other and denote a fluoroalkyl group, an alkyl group or a phenyl group.

2. A lithium salt comprising a chemical structure represented by the following general formula (2):

[Chemical Formula 2]

$$R_1-\underset{\underset{O}{\overset{O}{\|}}}{S}-N^--\underset{\underset{\underset{\underset{R_2}{|}}{\underset{S}{|}}}{\underset{O=S=O}{|}}}{\overset{Li^+}{|}}\overset{O}{\overset{\|}{P}}-X \quad \text{General Formula (2)}$$

in which $R_1$ and $R_2$ may be same or different from each other and denote a fluoroalkyl group, an alkyl group or a phenyl group; and "X" denotes a halogen atom.

3. A method for producing a lithium salt comprising a synthesis step of synthesizing a lithium salt which has a chemical structure represented by the following general formula (1):

[Chemical Formula 5]

$$R_1-\underset{\underset{O}{\overset{O}{\|}}}{S}-N^--\underset{\underset{\underset{\underset{R_2}{|}}{\underset{S}{|}}}{\underset{O=S=O}{|}}}{\overset{Li^+}{|}}\overset{O}{\overset{\|}{P}}-N^--\underset{\underset{O}{\overset{O}{\|}}}{S}-R_3 \quad \text{General Formula (1)}$$

in which $R_1$ to $R_3$ may be same or different from each other and denote a fluoroalkyl group, an alkyl group or a phenyl group, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) to (3-3):

[Chemical Formula 3]

$$R_1-\underset{\underset{O}{\overset{O}{\|}}}{S}-\overset{Li^+}{N^-}-H \quad \text{General Formula (3-1)}$$

$$R_2-\underset{\underset{O}{\overset{O}{\|}}}{S}-\overset{Li^+}{N^-}-H \quad \text{General Formula (3-2)}$$

$$R_3-\underset{\underset{O}{\overset{O}{\|}}}{S}-\overset{Li^+}{N^-}-H \quad \text{General Formula (3-3)}$$

in which $R_1$ to $R_3$ may be same or different from each other and denote a fluoroalkyl group, an alkyl group or a phenyl group; and wherein the material B for synthesizing a lithium salt has a chemical structure represented by the following general formula (4):

[Chemical Formula 4]

$$X-\underset{\underset{X}{|}}{\overset{\overset{O}{\|}}{P}}-X \quad \text{General Formula (4)}$$

in which "X" denotes a halogen atom.

4. A method for producing a lithium salt comprising a synthesis step of synthesizing a lithium salt which has a chemical structure represented by the following general formula (2):

[Chemical Formula 8]

$$R_1-\underset{\underset{O}{\overset{O}{\|}}}{S}-N^--\underset{\underset{\underset{\underset{R_2}{|}}{\underset{S}{|}}}{\underset{O=S=O}{|}}}{\overset{Li^+}{|}}\overset{O}{\overset{\|}{P}}-X \quad \text{General Formula (2)}$$

in which $R_1$ and $R_2$ may be same or different from each other and denote a fluoroalkyl group, an alkyl group or a phenyl group; and "X" denotes a halogen atom, wherein the lithium salt is obtained by using and reacting a material A for synthesizing a lithium salt and a material B for synthesizing a lithium salt;

wherein the material A for synthesizing a lithium salt has a chemical structure represented by the following general formulae (3-1) and (3-2):

[Chemical Formula 6]

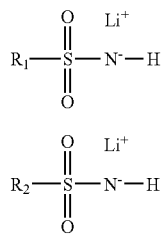

General Formula (3-1)

General Formula (3-2)

in which $R_1$ and $R_2$ may be same or different from each other and denote a fluoroalkyl group, an alkyl group or a phenyl group; and wherein the material B for synthesizing a lithium salt has a chemical structure represented by the following general formula (4):

[Chemical Formula 7]

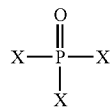

General Formula (4)

in which "X" denotes a halogen atom.

5. The method for producing a lithium salt according to claim 3, further comprising a purification step of removing a side reaction product generated by the synthesis step.

6. The method for producing a lithium salt according to claim 4, further comprising a purification step of removing a side reaction product generated by the synthesis step.

* * * * *